(12) United States Patent
Hernandez et al.

(10) Patent No.: US 9,970,879 B2
(45) Date of Patent: May 15, 2018

(54) APARATUS AND METHOD OF DETERMINING A REACTION SENSITIVITY THRESHOLD OF MATERIALS TO ELECROSTATIC DISCHARGE

(71) Applicant: The United States of America, as Represented by the Secretary, Department of Homeland Security, Washington, DC (US)

(72) Inventors: David Hernandez, Ato, NJ (US); David Hoey, Lynn Haven, FL (US); Joseph Eugene Chipuk, Jr., Charlottesville, VA (US); Benjamin Ostrow, Mays Landing, NJ (US)

(73) Assignee: The United States of America, as represented by the Secretary of Homeland Security, Washington, DC (US)

( * ) Notice: Subject to any disclaimer, the term of this patent is extended or adjusted under 35 U.S.C. 154(b) by 85 days.

(21) Appl. No.: 14/863,090

(22) Filed: Sep. 23, 2015

(65) Prior Publication Data
US 2016/0091430 A1    Mar. 31, 2016

Related U.S. Application Data

(60) Provisional application No. 62/055,015, filed on Sep. 25, 2014.

(51) Int. Cl.
*G06K 9/00*    (2006.01)
*G01N 21/67*   (2006.01)
*G01N 33/22*   (2006.01)

(52) U.S. Cl.
CPC .......... *G01N 21/67* (2013.01); *G01N 33/227* (2013.01)

(58) Field of Classification Search
CPC ............................ G01N 21/67; G01N 33/227
(Continued)

(56) References Cited

U.S. PATENT DOCUMENTS

| 6,889,903 | B1 * | 5/2005  | Koenck  | G06K 7/10633 |
|           |      |         |         | 235/462.01   |
| 9,202,145 | B2 * | 12/2015 | Guymon  | G06K 9/78    |
| 2004/0234107 | A1 * | 11/2004 | Machida | G06F 3/03547 |
|           |      |         |         | 382/107      |

OTHER PUBLICATIONS

Simpson et al. (LLNL Small-Scale Static Spark Machine: Static Spark Sensitivity Test, Aug. 23, 1999).*

(Continued)

*Primary Examiner* — Farhana Hoque
(74) *Attorney, Agent, or Firm* — Lavanya Ratnam; Trenton Roche; William Washington

(57) ABSTRACT

A method and apparatus for determining the sensitivity to electrostatic discharge (ESD) of energetic and volatile samples. The method and apparatus include an optical detector configured to detect the optical light intensity from an ESD event with time resolution less than 15 microseconds. The optical light intensity is integrated to obtain an integrated light intensity. The method and apparatus further include processing circuitry configured to determine whether the ESD event is a "Go" event, wherein the energetic material undergoes decomposition generating additional light in addition to light generated by the ESD event itself, or the ESD event is a "No-Go" event without decomposition of the energetic/volatile material. The integrated light intensity threshold between "Go" and "No-Go" events is determined using a statistical distribution of inert sample measurements.

15 Claims, 6 Drawing Sheets

(58) Field of Classification Search
USPC .......................................... 324/71.1; 382/100
See application file for complete search history.

(56) References Cited

OTHER PUBLICATIONS

Simpson, et al., LLNL Small-Scale Static Spark Machine: Static Spark Sensitivity Test, pp. 1-17, Sep. 23, 1999, Lawrence Livermore National Laboratory (U.S. Department of Energy), http://www.llnl.gov/tid/Library.html, https://library-ext.llnl.gov/.†

* cited by examiner
† cited by third party

APARATUS AND METHOD OF DETERMINING A REACTION SENSITIVITY THRESHOLD OF MATERIALS TO ELECROSTATIC DISCHARGE

BACKGROUND

Field

This disclosure relates to small scale safety testing of materials and a method and instrument to objectively differentiate between reaction and non-reaction events. This is important to Government and commercial explosive manufacturers, explosive testing laboratories, as well as international testing groups responsible for determining if materials are safe for transport.

Description of the Related Art

Electrostatic discharge (ESD) is one of the most frequent and the least characterized causes of accidental explosions of energetic materials. To have reliable data on electrostatic spark sensitiveness of energetic materials is thus a critical component within the manufacturing process, in research and development, physical processing, handling, storage, and transportation.

ESD testing is used to determine the response of explosive material, commonly energetic, when subjected to various levels of electrostatic discharge energy. The test sample is placed on a holder and electrostatic energy, which is conventionally stored in a charged capacitor, is discharged through the test sample.

The electric spark sensitivity or electrostatic discharge sensitivity of an explosive may be defined as the amount of energy of an electric spark discharge that could cause either initiation, ignition or, depending on the level of electrostatic discharge energy, explosion of an energetic sample under test.

Presently, electrostatic discharge sensitivity tests and apparatuses in current use are designed and fabricated by the laboratories for their own use to evaluate in-process hazards. However, the basic components of an ESD tester include a high voltage supply, hardware for varying capacitance, an electrical charging circuit, a triggering circuit, an electrode assembly and an electrostatic voltmeter to measure the voltage. Approximately 10-30 mg of the sample is placed on a grounded conductive surface to ensure the discharge passes through the material and various methods are used to determine if a reaction has occurred. Differentiating between electrostatic discharge events above (i.e., "Go" events) and below (i.e., "No-Go" events) energy levels, the observation that a reaction has occurred in the material has conventionally required subjective determinations by users of the testing apparatus. This invention reduces or eliminates the subjective nature of these measurements and is important for developing a uniform standard among multiple laboratories determining the electrostatic-discharge sensitivity of materials.

Historically, users have observed tests and documented smoke, sample consumed, jetting (visible ejection of material), spark, flame trace (charred residue or burn marks), flash/flame, audible pop, load report/explosion, and/or hardware damage for every test completed. Given that the testing involves violent events in the routine operation, discernment of reactions is problematic. Additionally, human observation deteriorates based upon fatigue, distractions, and operating procedures. The human observation method of differentiating between "Go" and "No-Go" events has the advantage of requiring low upfront cost. However, this method is subjective and inconsistent because it relies on observation and memory; Therefore it can yield inconsistent results. Moreover, user observation in ESD testing contributes to physiological damage of the user's eyes due to repeated ultraviolet light exposure. Conventional test procedures require direct observation of numerous trials. Damage affects due to continued and repeated exposure to ultraviolet light could cause permanent damage, making users' observation an undesirable form of ESD testing.

Gas detection can also be used for differentiating between "Go" and "No-Go" events. Most explosive materials are nitrogen containing organic molecules that include carbon, hydrogen and oxygen. Decomposition products from these materials are carbon dioxide, carbon monoxide, nitrogen, and water. Gas analyzers have evolved to enable the quantification and identification of carbon dioxide and carbon monoxide as decomposition products. Many factors affect detection and resolution of gas analyzers such as mass spectrometers. Specifically, ambient air includes fluctuating amounts of each of the gases, humans exhale some of the products, and any fuel burning operation (gas/propane engines) will produce the same products. Although the gas-detection method provides quantifiable metrics, the resolution of the gas-detection method depends on environmental conditions, and the method requires direct access to the sample chamber during testing, which may obscure the sample from other detection methods. Moreover, the gas-detection of carbon dioxide and carbon monoxide method only works for organic explosives.

In addition to the gas-detection and user-observation methods, Sandia National Laboratories has developed a slow-camera method for differentiating between "Go" and "No-Go" events. There, a digital single-lens reflex camera (D-SLR) is programmed with a long duration shutter that captures all light emitted during a one second exposure of the D-SLR camera during which an ESD event occurs. The images reveal a sort of historical record of light that can be reviewed by an observer and determine whether or not a reaction was detected. The major obstacle to this method is that it relies on a subjective decision that arbitrarily rules out light emitted from system components (sparks from burning pieces of the ESD needle called "flyers"). Although the slow-camera method produces good quality images that can be archived and re-referenced, this method, like the user-observation method, relies on subjective decisions.

Safety Management Services Inc. (SMS) uses an alternative high-speed camera method for differentiating between "Go" and "No-Go" events. As instrumentation progresses, high speed video methods have been adapted to capture testing events. The added benefit of temporal information allows testers to see latent and duration information not included in the open shutter technique pioneered by Sandia National Laboratories. SMS has developed a semi-automated system to detect reactions, but still relies upon user input for reaction detection. The SMS system requires user definitions of positive reactions based upon features of spark, flame, and resultant buoyancy of particles and smoke and is thus still subjective.

Thus, conventional electrostatic safety testing of material involves observations of in-process hazards and subjective determinations of sensitivity. Tests are conventionally carried out with a human observer attempting to discern between a spark from electrostatic discharge (ESD) and decomposition of a material that may add light, sound, or smoke to the reaction. Advances have been made in the automation of these subjective responses, yet still require user input and baseline reference assessments. User fatigue, memory interference, and perspective affect the data of subjective testing and have relegated the data to only be valid when relatively compared to a well characterized standard.

There is a clear and distinct need to develop a method and apparatus that can consistently and reproducibly resolve the difference between non-reaction and reaction events without user input.

SUMMARY

An electrostatic discharge (ESD) sensitivity determination apparatus, including: an optical detector detecting light intensity data representative of optical light intensity of an ESD event with a time resolution of at least 20 microseconds; a trigger signaling when the ESD event occurs, light intensity; and processing circuitry configured to calculate a Go/No-Go threshold from a statistical distribution of the light intensity data of ESD events using a inert sample; light intensity; and determine the accumulation of light intensity of ESD events using a real sample exceeds when the count of Go events can be discerned from a no-go event.

BRIEF DESCRIPTION OF THE DRAWINGS

A more complete understanding of this disclosure is provided by reference to the following detailed description when considered in connection with the accompanying drawings, wherein.

DETAILED DESCRIPTION

Described herein are embodiments of an apparatus and method for consistently and reproducibly resolving the difference between non-reaction and reaction events without user input. Additionally, the embodiments of the apparatus and method can capture and account for the testing equipment's contribution to reactions, and provide greater safety to testers as well as provide consistent and reliable results.

Figure 3:
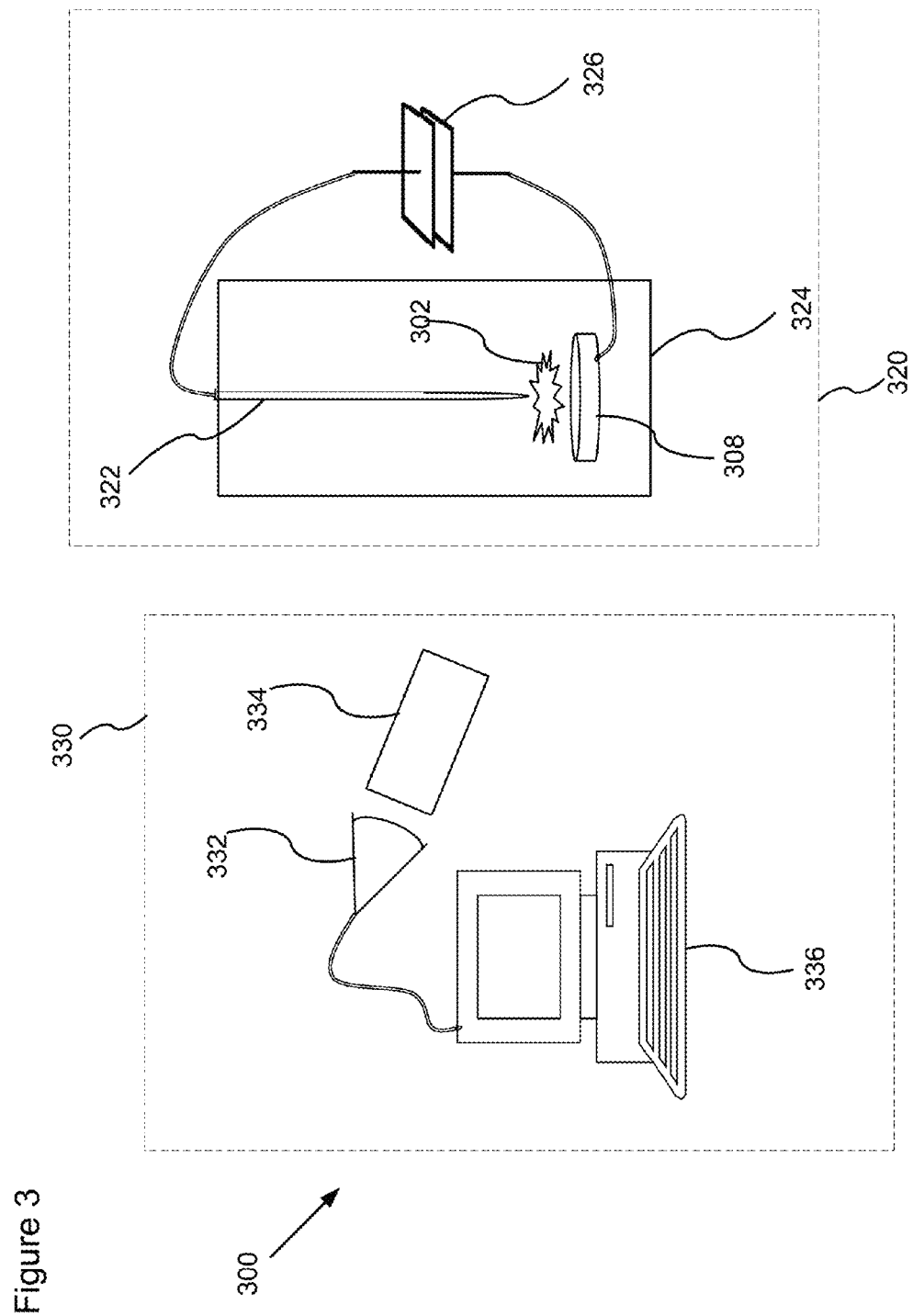
FIG. 3 shows a schematic of one embodiment of an apparatus for determining the ESD sensitivity threshold of a sample.

Referring now to the drawings, wherein like reference numerals designate identical or corresponding parts throughout the several views, FIG. 3 illustrates an embodiment of an apparatus for differentiating whether an electrostatic discharge (ESD) event results in decomposition of a sample (i.e., a "Go" event) or not (i.e., a "No-Go" event). In the ESD tester, the electrostatic discharge 302 occurs through a sample 308 and emits light. Within the camera, the light intensity is then collected and filtered through optical elements 334 which then focuses the collected light onto an optical detector 332 and the measured light intensity from the event is then stored and processed using a data-acquisition-and-processing system 336.

Figure 1:
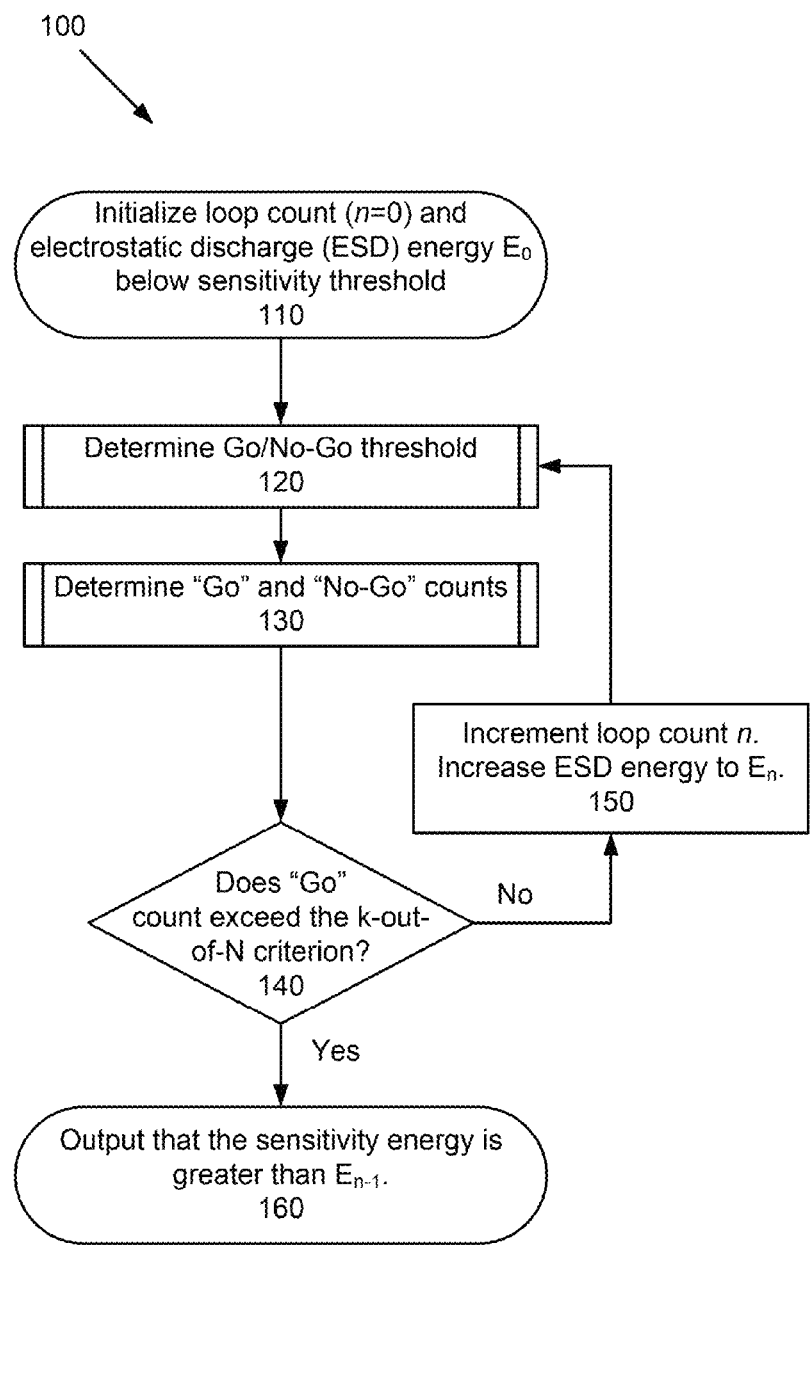
FIG. 1 shows a flow diagram of one embodiment of a method of determining an electrostatic discharge (ESD) sensitivity threshold of a sample.

FIG. 1 shows an ESD-sensitivity method 100 of determining an ESD sensitivity threshold for the sample 308. The sensitivity threshold is determined by starting at a low ESD energy, below the sensitivity threshold, and incrementally increasing the ESD energy until k-out-of-N ESD events are "Go" events. Then the sensitivity threshold is recorded as the incremental ESD energy immediately before the k-out-of-N criterion is satisfied (i.e., the ESD sensitivity threshold is $E_{n-1}$ where $E_n$ is the ESD energy corresponding to satisfying the k-out-of-N criterion). Conventionally, the k-out-of-N criterion is satisfied when at least 1 out of 20 ESD events results is a "Go" event.

Figure 5:
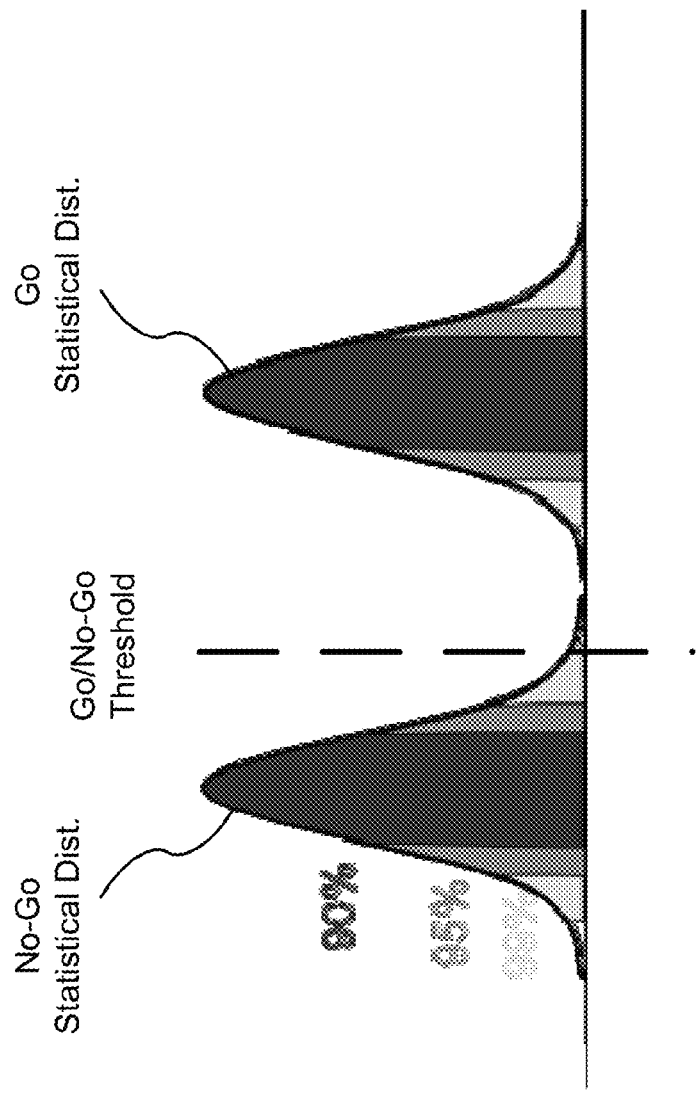
FIG. 5 shows a figure illustrating the determination of a Go/no-go threshold between a no-go statistical distribution and a go statistical distribution.

The ESD-sensitivity method 100, shown in FIG. 1, begins, at step 110, by initializing the ESD energy below the sensitivity threshold. Next, at process 120 of ESD-sensitivity method 100, a Go/No-Go threshold is determined. In one embodiment, a inert sample is placed in the apparatus and a series of ESD events are conducted to calibrate the Go/No-Go threshold by, e.g., determining the statistical variation of the detected light for a series ESD events and setting the Go/No-Go threshold such that, to a predetermined statistical certainty, ESD events below the Go/No-Go threshold are No-Go events. For example, FIG. 5 shows a statistical distribution for "Go" events and "No-Go" events with a Go/No-Go threshold chosen such that 99.5% of No-Go events generate light less than the Go/No-Go threshold.

Outlier events can occur for these calibration measurements using inert samples when an ESD event results in flyers. Flyers can results from sparks and burning pieces of an ESD needle 322. These flyers often have a longer lifetime than both the light directly generated by ESD and light from decomposition of the sample 308. Therefore, the effect of outlier events due to flyers can be minimized by narrowing the temporal integration window for light detected from each ESD event.

Next, at process 130 of ESD-sensitivity method 100, "Go" and "No-Go" determinations are performed for a series of NESD events using the actual sample 308 rather than a inert sample.

In one embodiment, the energy of the ESD event is determined by the energy stored in a capacitor 326, wherein ESD causes the energy from the capacitor 326 to be discharged into the sample 308. The energy stored in the capacitor 326 is given by $$E = \frac{1}{2}CV^2,$$

where C is the capacitance of the capacitor 326 and V is the voltage stored on the capacitor 326. The energy stored in the capacitor 326 can be modified either by changing the capacitance or by changing the voltage. Conventionally, the stored energy is incremented by increasing the capacitance C of the capacitor 326 while maintaining a constant voltage V. Capacitance values may are variable and must be sufficient to allow capture of both go and no-go events. In one embodiment, the capacitance value of the capacitor can be adjusted within the range 0.1 μF to 50 μF. After incrementing the ESD energy the loop begins again at process 120.

Figure 2:
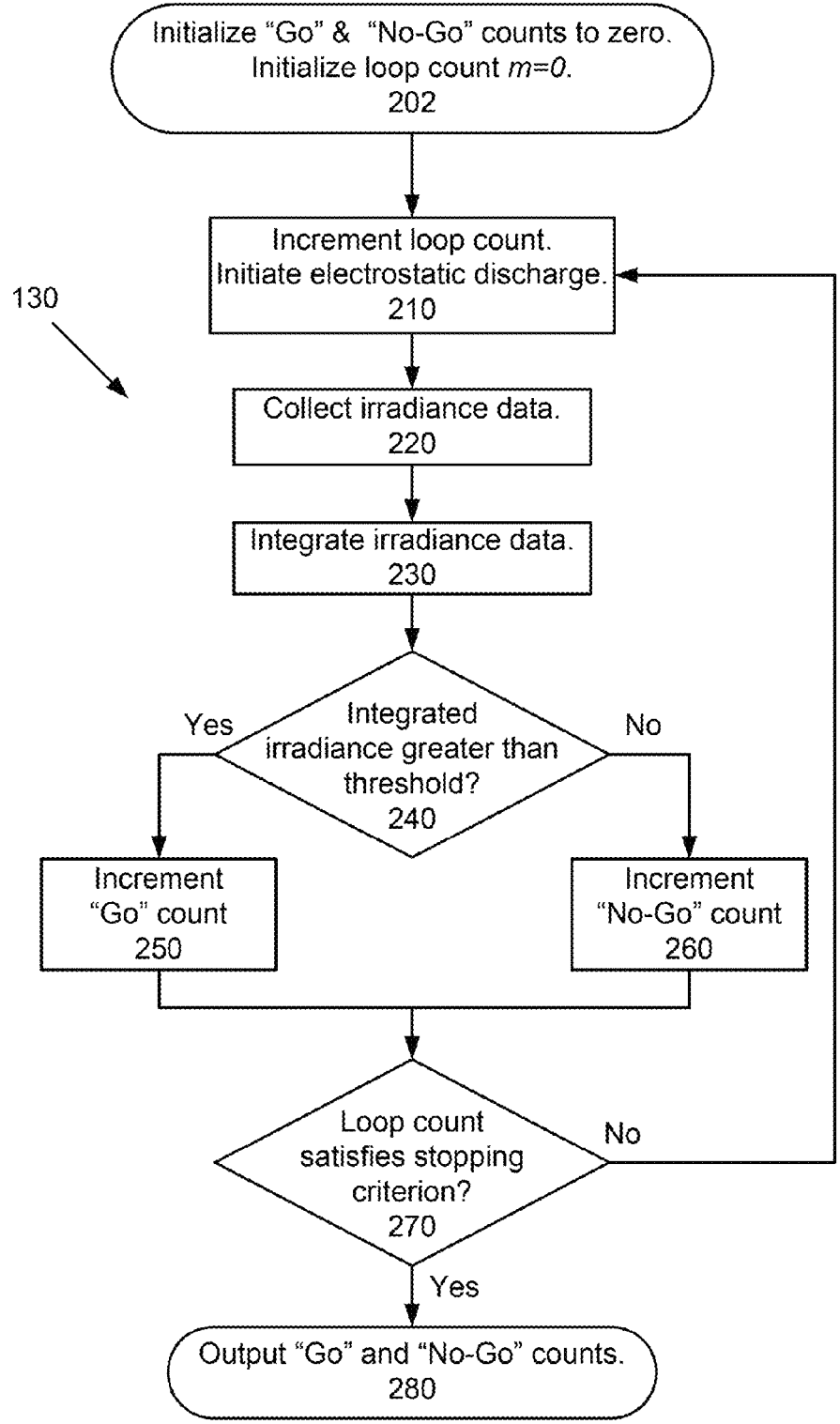
FIG. 2 shows a flow diagram of one embodiment of a process for determining the number of "Go" and "No-Go" counts for a series of ESD events.

FIG. 2 shows a method of the Go/No-Go determination process 130. Process 130 begins, at step 202, by initializing each of the "Go," "No-Go," and loop counts to zero.

In a first step 210 of the iterative loop, the loop count is incremented and ESD is initiated through the sample 308 by, e.g., bringing the needle 322 into proximity with the ground plane.

Next at step 220 of process 130, the light intensity from the ESD event is measured, and at step 230 the measured irradiance is integrated. In one embodiment using a camera as an optical detector the light intensity is integrated both spatial and temporally. In another embodiment using a photodetector, such as a photodiode or photomultiplier tube, wherein the spatial integration is performed during the detection process, the light intensity is integrated temporally at step 220.

If, at step 240 of process 130, the integrated light intensity is determined to be greater than the ESD sensitivity threshold, then a "Go" event is determined to have occurred and the "Go" count is incremented by one, at step 250. Otherwise, a "No-Go" event is determined to have occurred and the "No-Go" count is incremented by one, at step 260.

At step 270, the loop count m is compared to the total number N of ESD events. If the loop count m is less than N then the loop returns to step 210 to repeat the loop. Otherwise the loop truncates outputting the resultant "Go" and "No-Go" counts.

FIG. 3, as pointed out above, shows a schematic drawing of the ESD testing apparatus 300 according to one embodiment of the disclosure. The apparatus 300 includes an ESD unit 320 and an optical detection unit 330. The ESD unit 320 includes the capacitor 326 which stores the energy for the ESD event. A first terminal of the capacitor 326 is electrically connected to a first conducting surface positioned on a first side of the sample 308. A second terminal of the capacitor 326 is electrically connected to a second conducting surface (e.g., the needle 322) that is near a second surface of the sample 308 diametrically opposed to the first surface of the sample 308. In one embodiment, the voltage potential of the needle 322 is greater than the voltage potential of the ground plane. In another embodiment, the voltage potential of the needle 322 is less than the voltage potential of the ground plane. As the second conducting surface is brought into closer proximity to the sample 308 and the first conducting surface ESD initiates as a spark 302 that travels through the sample 308. A protective barrier 324 can surround the sample 308 and the first and second conducting surfaces protecting users in the space exterior to a protective barrier 324 from the high voltage inside the protective barrier 324. The protective barrier 324 can include a window such that light from the ESD event propagates to the optical elements 334.

The optical elements 334 can include lenses, spatial filters, and wavelength filters. These optical elements can be used to isolate the light intensity of the ESD event from background signals. The optical elements 334 also focus light from the ESD event onto the optical detector 332, and the optical detector 332 measures the light intensity of the ESD light incident on the optical detector 332. Further, background subtraction can be performed on the measured light intensity. The measured light intensity is transmitted to and recorded using a data acquisition and processing system 336. The optical detector 332 and data acquisition and processing system 336 can be triggered to record the measured light intensity using a signal from the ESD event. The signal from the ESD event can originate from light, motion, sound waves, current from the capacitor 326, radio frequency transients, and other electromagnetic signals indicative of the ESD events. In one embodiment, the trigger signal is derived directly from the light from the ESD event.

In another embodiment, the trigger signal is derived from the electrical signals originating from the capacitor (e.g., the current flowing into the needle 322). In one embodiment, the data acquisition and processing system 336 is used both to acquire the optical signal data and also to control the energy stored in the capacitor 326 and the ESD event.

Figure 6:
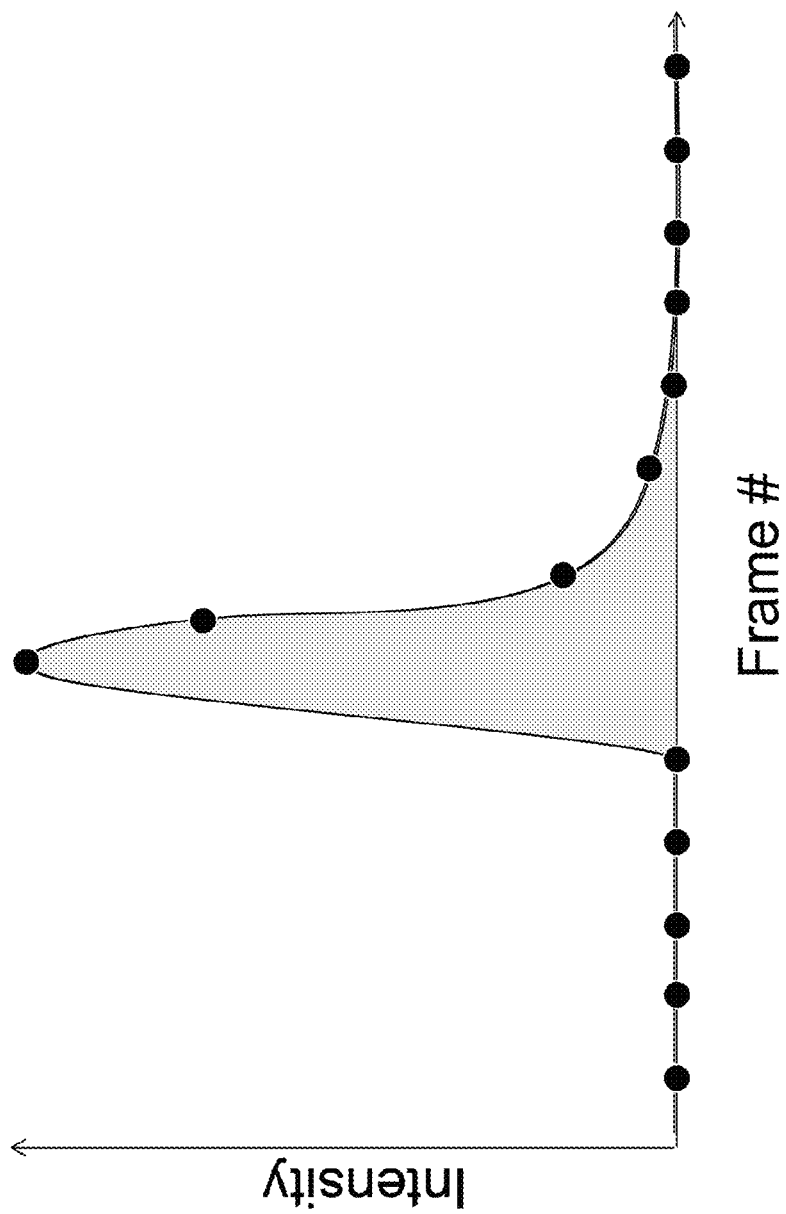
FIG. 6 shows a plot of the spatially-integrated intensity/light intensity (vertical axis) of an ESD event plotted versus the time and frame number (horizontal axis).

In one embodiment, the optical detector 332 is a high-speed digital camera capable of acquiring 75,000 frames per second. For example, the optical detector 332 can be a Fastcam SA4 camera distributed by Photron USA, Inc. The high-speed digital camera can be triggered using an SP1005 near IR trigger distributed by CAL-AV Labs, Inc. The data acquisition and processing system 336 can use ImageJ software provided by the National Institute of Health to integrate light intensity of each frame by summing over all of the pixels of the respective frames. FIG. 6 shows a temporal profile of light intensity of a inert sample ESD event, wherein each dot shows light intensity of a given frame from the high-speed camera. Lab-View software can be used to transfer the integrated intensity/light intensity form the Image) format into an Excel software format. The data quality can be improved by calibrating the camera and performing background subtraction. Additionally, in one embodiment, the temporal profile of light intensity from the ESD event can be integrated over a predetermined time window to yield a single intensity/light intensity value per ESD event. In one embodiment, the Go/No-Go threshold is determined using Excel software by processing the inert sample data according to process 120. Using the Go/No-Go threshold, the sensitivity threshold is determined by processing ESD sample data according to the method 100 including process 130.

The optical detector 332 can be implemented using a photodetector such as a semiconductor photodiode, a vacuum photodiode, an avalanche photodiode, a micro channel plate, photo-multiplier tube, or the like. The signal from the photodiode can be amplified using a trans-impedance amplifier, a low-noise pre-amplifier, a current amplifier, charge amplifier, or the like. In one embodiment, the time resolution of this photodetector signal can be several orders of magnitude greater than the time resolution achievable with high-speed cameras. The temporal profile of light intensity of the ESD event can then be integrated in hardware (e.g., using a box-car integrator) or in software after the temporal intensity/light intensity data has been recorded using the data acquisition and processing system 336 (e.g., by integrating the time-series data corresponding to measured temporal profile of light intensity of the ESD event). Using a high-speed photodetector and a boxcar integrator or high speed data acquisition card, such as a NI PCI-6110 PCI card from National Instruments Corporation, the apparatus 300 becomes much less expensive than a high-speed camera implementation while still achieving automated operation that enables consistent and reliable performance. Additionally, in all implementations, the data quality can be improved by calibrating the detectors and performing background subtraction. The data acquisition and processing system 336 records light intensity of the ESD event using, e.g., a central processing unit and a non-transient computer readable memory. The trigger for the optical detector 332 and the data acquisition and processing system 336 can be any of an acoustic, infrared, motion-detection, or manual trigger.

In one embodiment, the optical detection unit 330 of the ESD testing apparatus 300 includes a combination of commercially available equipment, including: an electrostatic discharge system used in safety testing; a high speed digital camera system capable of 75,000 frames per second or more with accompanying software for data capture and rendering; a triggering system; software programmed to analyze an image to determine cumulative light intensity; and software that is programmed to automatically check folders for appropriate files and to perform simple calculations. The high speed video camera can use 35-200 mm primary or micro/macro lenses. Telephoto lenses may also be used. At 75,000 frames per second, an electrostatic discharge may persist for as short as 3 frames of the camera (~40 µs). In one embodiment the high-speed camera can collect and store at least 100 frames, including a real-time operational baseline collected 30 or more frames prior to the event for each ESD event. The baseline provides background information and reduces error associated with fluctuations in detector performance, spurious light, and optic aberrations.

The optical detection unit 330 of the ESD testing apparatus 300 can use any triggering system such as acoustic, infrared, motion detection, or manual triggering as long as the baseline and event frames are captured. The ESD unit of the ESD testing apparatus 300 can use any electrostatic discharge testing system that provides an optical pathway to detect light from the ESD event. The data acquisition and processing system 336 can use any software that determines and records the cumulative light intensity.

Figure 4:
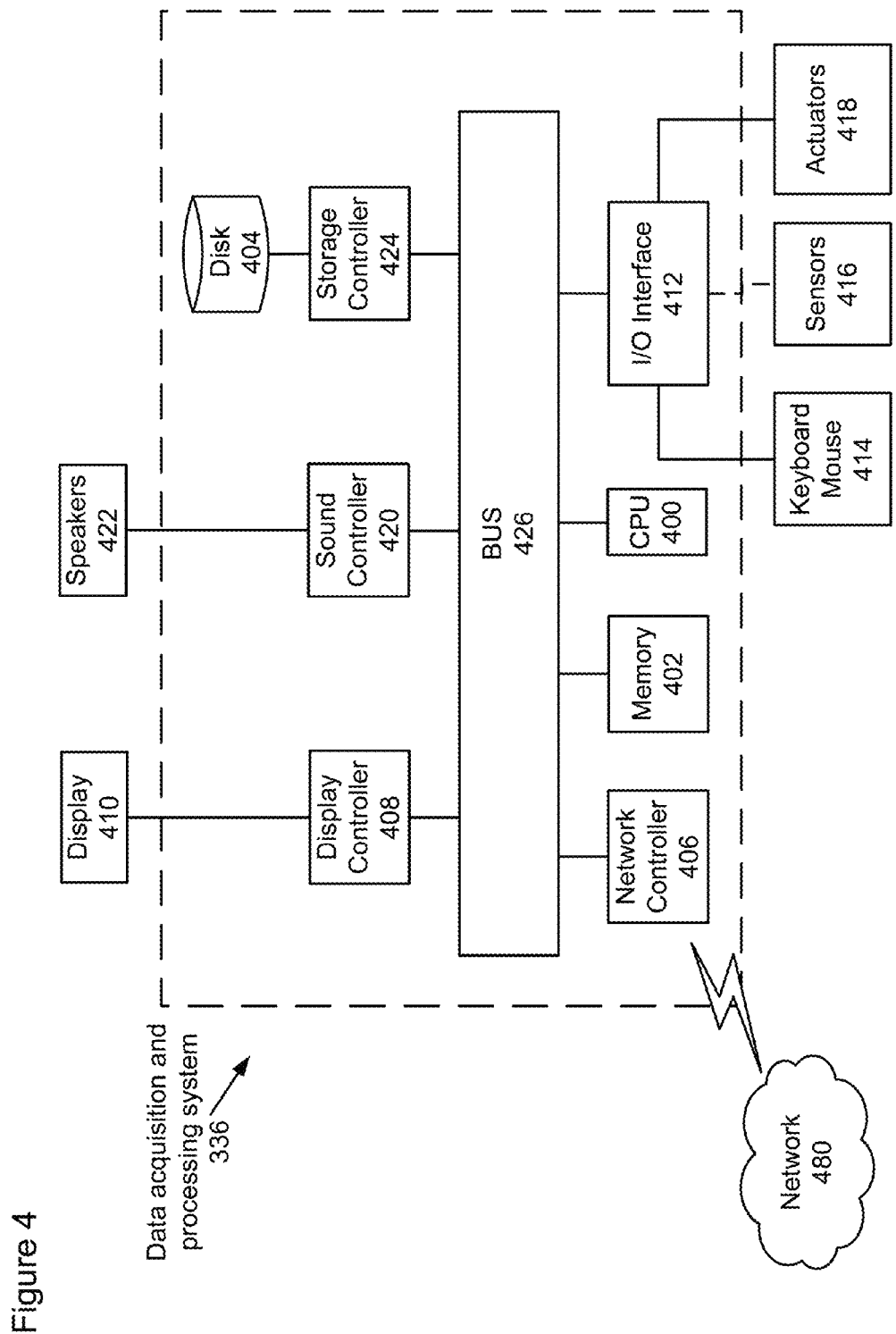
FIG. 4 shows a schematic of one embodiment of a data acquisition and processing system.

Next, a hardware description of the data acquisition and processing system 336 according to exemplary embodiments is described with reference to FIG. 4. In FIG. 4, the data acquisition and processing system 336 includes a CPU 400 which performs the processes described above including method 100 and the integration of the acquired intensity/light intensity data. The process data and instructions may be stored in memory 402. These processes and instructions may also be stored on a storage medium disk 404 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the Data acquisition and processing system 336 communicates, such as a server or computer.

Further, the claimed advancements may be provided as a utility application, background daemon, or component of an operating system, or combination thereof, executing in conjunction with CPU 400 and an operating system such as Microsoft Windows 7, UNIX, Solaris, LINUX, Apple MAC-OS and other systems known to those skilled in the art.

CPU 400 may be a Xenon or Core processor from Intel of America or an Opteron processor from AMD of America, or may be other processor types that would be recognized by one of ordinary skill in the art. Alternatively, the CPU 400 may be implemented on an FPGA, ASIC, PLD or using discrete logic circuits, as one of ordinary skill in the art would recognize. Further, CPU 400 may be implemented as multiple processors cooperatively working in parallel to perform the instructions of the inventive processes described above.

The data acquisition and processing system 336 in FIG. 4 also includes a network controller 406, such as an Intel Ethernet PRO network interface card from Intel Corporation of America, for interfacing with network 400. As can be appreciated, the network 400 can be a public network, such as the Internet, or a private network such as an LAN or WAN network, or any combination thereof and can also include PSTN or ISDN sub-networks. The network 400 can also be wired, such as an Ethernet network, or can be wireless such as a cellular network including EDGE, 3G and 4G wireless cellular systems. The wireless network can also be Wi-Fi, Bluetooth, or any other wireless form of communication that is known.

The data acquisition and processing system 336 further includes a display controller 408, such as a NVIDIA GeForce GTX or Quadro graphics adaptor from NVIDIA Corporation of America for interfacing with display 410, such as a Hewlett Packard HPL2445w LCD monitor. A general purpose I/O interface 412 interfaces with a keyboard and/or mouse 414. Additionally, the I/O interface could include a PCI data acquisition card such as the NI PCI-6110 from National instruments Corporation or other data acquisition recognized by one of ordinary skill in the art. The I/O interface 412 can include sensor inputs 416 such as analog signals from a current and/or voltage sensor measuring the current (e.g., a Rogowski coil or the like) and/or voltage at the needle 322. Also, the I/O interface 412 can include output signals for controlling actuators 410, e.g., controlling the height of the needle 322 or triggering an ESD event via a high-voltage low-current spike on the needle 322 to initiate ESD breakdown. The general purpose I/O interface also connects to a variety of peripherals including printers and scanners, such as an OfficeJet or DeskJet from Hewlett Packard.

A sound controller 420 is also provided in the Data acquisition and processing system 336, such as Sound Blaster X-Fi Titanium from Creative, to interface with speakers/microphone 422 thereby providing sounds and/or music.

The general purpose storage controller 424 connects the storage medium disk 404 with communication bus 426, which may be an ISA, EISA, VESA, PCI, or similar, for interconnecting all of the components of the Data acquisition and processing system 336. A description of the general features and functionality of the display 410, keyboard and/or mouse 414, as well as the display controller 408, storage controller 424, network controller 406, sound controller 420, and general purpose I/O interface 412 is omitted herein for brevity as these features are known.

While certain implementations have been described, these implementations have been presented by way of example only, and are not intended to limit the teachings of this disclosure. Indeed, the novel methods, apparatuses and systems described herein may be embodied in a variety of other forms; furthermore, various omissions, substitutions and changes in the form of the methods, apparatuses and systems described herein may be made without departing from the spirit of this disclosure.

The invention claimed is:

1. An electrostatic discharge (ESD) sensitivity apparatus, comprising:
   an optical detector detecting light intensity data representative of an optical light intensity of an ESD event, the light intensity data having a time resolution of less than or equal to 20 microseconds;
   a trigger generator generating a trigger signal when the ESD event occurs, and the trigger signal determining the time interval over which the optical detector detects the light intensity data; and
   processing circuitry configured to calculate a Go/No-Go threshold from a statistical distribution of the light intensity data of the ESD events using an inert sample;
      determine a count of Go events when the light intensity data of ESD events using a real sample exceeds the Go/No-Go threshold; and determine an ESD energy of the ESD events using the real sample exceeds a sensitivity threshold when the count of Go events exceeds a predetermined Go-count threshold.

2. The ESD sensitivity apparatus according to claim 1, wherein
the optical detector is a high-speed camera having a frame rate of at least 75,000 frames per second and capable of recording at least 100 consecutive frames.

3. The ESD sensitivity apparatus according to claim 2, wherein
the high-speed camera records at least 30 frames preceding the ESD event triggering the high-speed camera.

4. The ESD sensitivity apparatus according to claim 1, wherein
the optical detector is one of a photodiode, avalanche photodiode, and a photomultiplier tube.

5. The ESD sensitivity apparatus according to claim 1, further comprising:
a boxcar integrator integrating, in time, the light intensity data within a predetermined time window.

6. The ESD sensitivity apparatus according to claim 1, wherein
the trigger is initiated by one of an optical signal from the ESD event, an acoustic signal from the ESD event, an electrical signal from the ESD, and a manual trigger signal.

7. The ESD sensitivity apparatus according to claim 1, wherein
the Go/No-Go threshold is determined to maintain the number of false "Go" events below a predetermined statistical level according to the statistical distribution of the light intensity data of ESD events using an inert sample.

8. The ESD sensitivity apparatus according to claim 1, further comprising:
a storage capacitor;
a ground plane electrical connected to a first terminal of the storage capacitor;
a needle electrical connected to a second terminal of the storage capacitor; and
a needle actuator configured to adjust the proximity between the needle and the ground plane, wherein
the ground plane and the needle are arranged such that when the needle is brought within close proximity to the ground plane and a sample is arranged on the ground plane the ESD event will cause electrical current to flow through the sample.

9. A method of determining the sensitivity of a sample to electrostatic discharge (ESD), the method comprising:
positioning a sample between a ground plane electrically connected to a first terminal of a storage capacitor and a needle electrically connected to a second terminal of the storage capacitor;
causing a greater voltage potential in the needle than in the ground plane;
adjusting the space between the needle and the ground plane until an ESD event occurs;
focusing light from the ESD event onto an optical detector connected to processing circuitry configured to perform data acquisition and data processing on light intensity data representative of the ESD event;
recording light intensity data representative of the light intensity on the optical detector from the ESD event; and statistically analyzing the light intensity data from a plurality of ESD events on an inert sample to determine a Go/No-Go threshold.

10. The method according to claim 9, further comprising:
Comparing the light intensity data from the ESD event at a first ESD energy on an energetic-material sample;
determining that the ESD event on the energetic-material sample is a "Go" event when the corresponding light intensity data exceeds the Go/No-Go threshold; and
determining that the electrostatic discharge event on the energetic-material sample is a "No-Go" event when the corresponding light intensity data does not exceed the Go/No-Go threshold.

11. The method according to claim 10, further comprising:
determining that the first ESD energy exceeds a sensitivity threshold of the energetic-material sample when the number of "Go" events exceeds a predetermined Go-count threshold, otherwise the first ESD energy does not exceed the sensitivity threshold of the energetic-material sample;
increasing the ESD energy by a predetermined energy increment from the first ESD energy to a second ESD energy when the first ESD energy does not exceed the sensitivity threshold of the energetic-material sample; and
repeating, at the second ESD energy and increasingly greater ESD energies until the sensitivity threshold of the energetic-material sample is exceeded, the steps of recording light intensity data of the ESD events, statistically analyzing the light intensity data of the ESD events on the inert sample to determine a Go/No-Go threshold, and comparing the light intensity data of the ESD events on the energetic-material sample to determine whether the second ESD energy exceeds a sensitivity threshold of the energetic-material sample.

12. The method according to 9, wherein the optical detector used in the recording of the light intensity data of the ESD event is a high-speed camera configured to acquire light intensity images at a frame rate of at least 75,000 frames per second and record at least 100 consecutive frames, wherein a sufficient amount of background frames, notionally 30 or more, to allow background subtraction.

13. The method according to 9, wherein the optical detector used in the recording of the light intensity data of the ESD event is one of a photodiode, avalanche photodiode, and a photomultiplier tube.

14. The method according to 13, wherein the optical detector further includes a boxcar integrator integrating, in time, the light intensity data within a predetermined time window.

15. An electrostatic discharge (ESD) sensitivity apparatus, comprising:
optical-detection means for detecting light intensity data representative of optical light intensity of an ESD event with a time resolution of at least 20 microseconds;
triggering means for generating a trigger signal when the ESD event occurs, and the trigger signal determining the time interval over which the optical detector detects the light intensity data; and
processing means for
calculating a Go/No-Go threshold from a statistical distribution of the light intensity data of ESD events using an inert sample;
determining a count of Go events when the light intensity data of ESD events using a real sample exceeds the Go/No-Go threshold; and determining an ESD energy of the ESD events using a real sample exceeds a sensitivity threshold when the count of Go events exceeds a predetermined Go-count threshold.

\* \* \* \* \*